United States Patent [19]
Li et al.

[11] Patent Number: 6,021,679
[45] Date of Patent: Feb. 8, 2000

[54] PROBE FOR SLURRY GAS SAMPLING

[75] Inventors: Leping Li, Poughkeepsie, N.Y.; James A. Gilhooly, Saint Albans; Clifford O. Morgan, III, Burlington, both of Vt.; Cong Wei, Poughkeepsie, N.Y.; Werner Moser, Gebertingen; Matthias Kutter, Staefa, both of Switzerland; Joseph Knee, Cromwell, Conn.; Walter Imfeld, Hombrechtikon, Switzerland; Bruno Greuter, Wolfhausen, Switzerland; Heinz Stuenzi, Hombrechtikon, Switzerland

[73] Assignee: International Business Machines Corporation, Armonk, N.Y.

[21] Appl. No.: 09/129,102

[22] Filed: Aug. 4, 1998

[51] Int. Cl.[7] ............................................. G01N 1/00
[52] U.S. Cl. ............................................. 73/863.23
[58] Field of Search ........................... 73/863.23, 864.34, 73/864.73, 864.81

[56] References Cited

U.S. PATENT DOCUMENTS

| | | | |
|---|---|---|---|
| 5,317,932 | 6/1994 | Westlake, III et al. | 73/864.73 |
| 5,442,970 | 8/1995 | Hutchins | 73/864.63 |
| 5,448,922 | 9/1995 | Kimbell et al. | 73/863.23 |
| 5,553,484 | 9/1996 | Bender et al. | 73/864.73 |

*Primary Examiner*—Robert Raevis
*Attorney, Agent, or Firm*—Alison D. Mortinger

[57] ABSTRACT

Device for in-situ collection of a gaseous reaction product from a polishing slurry as a workpiece, such as a semiconductor wafer, is being polished with the slurry, including a probe capable of being placed in contact with the slurry, the probe having a channel for transmitting the gaseous reaction product to an analyzer, a first hydrophobic membrane for allowing passage of the gaseous reaction product from the slurry to the channel, and means for directing a carrier gas through the channel.

12 Claims, 2 Drawing Sheets

PROBE FOR SLURRY GAS SAMPLING

FIELD OF THE INVENTION

This invention is directed to semiconductor processing and more particularly to the collection and sampling of gaseous products from slurry used in a chemical-mechanical polishing process.

BACKGROUND OF THE INVENTION

In the semiconductor industry, chemical-mechanical polishing (CMP) is used to remove a portion of a film deposited on a wafer. With CMP, a film is selectively removed from a semiconductor wafer by rotating the wafer against a polishing pad (or rotating the pad against the wafer, or both) with a controlled amount of pressure in the presence of a slurry. Monitoring and controlling the CMP process is difficult; such tasks including but not limited to (1) detecting when polishing should be stopped (i.e. the endpoint has been reached), (2) detecting particles in the slurry which cause scratching, (3) detecting chemical species for contamination control, or (4) understanding process chemistry, would all be desirable.

Such tasks as (1), (3), and (4) could be achieved by in-situ real time (i.e. while the wafer is being polished) slurry sampling and analysis of gaseous reaction products resulting from a reaction between the slurry and the layer(s) being polished on the wafer. However, a robust collection apparatus is needed, which is not affected by the slurry chemistry, does not interfere with the polishing, and enables sampling with a rapid response time.

SUMMARY OF THE INVENTION

It is therefore an object of the present invention to provide a collection system for gaseous reaction products in a slurry for use in in-situ real-time sampling and analysis.

Another object of the present invention is to provide for such a collection system which is not affected by the slurry chemistry.

Another object of the present invention is to provide for such a collection system that does not interfere with the polishing process.

Yet another object of the present invention is to provide for such a collection system that enables sampling with a rapid response time.

In accordance with the above listed and other objects, an apparatus for in-situ collection of a gaseous reaction product from a polishing slurry as a workpiece is being polished with the slurry, including a probe capable of being placed in contact with the slurry, the probe having a channel for transmitting the gaseous reaction product to an analyzer, a first hydrophobic membrane for allowing passage of the gaseous reaction product from the slurry to the channel, and means for directing a carrier gas through the channel is described.

BRIEF DESCRIPTION OF THE DRAWINGS

These and other features, aspects, and advantages will be more readily apparent and better understood from the following detailed description of the invention, in which.

DESCRIPTION OF THE PREFERRED EMBODIMENTS

The present invention is described herein in the context of chemical-mechanical polishing merely as a specific example, and is not meant to limit applicability of the invention to semiconductor technology. Those skilled in the art will understand that the invention is broadly applicable to any process in which it is desirable to have in-situ collection of a gaseous reaction product from a polishing slurry as a workpiece is being polished with the slurry, including a probe capable of being placed in contact with the slurry, the probe having a channel for transmitting the gaseous reaction product to an analyzer, a first hydrophobic membrane for allowing passage of the gaseous reaction product from the slurry to the channel, and means for directing a carrier gas through the channel.

Figure 1:
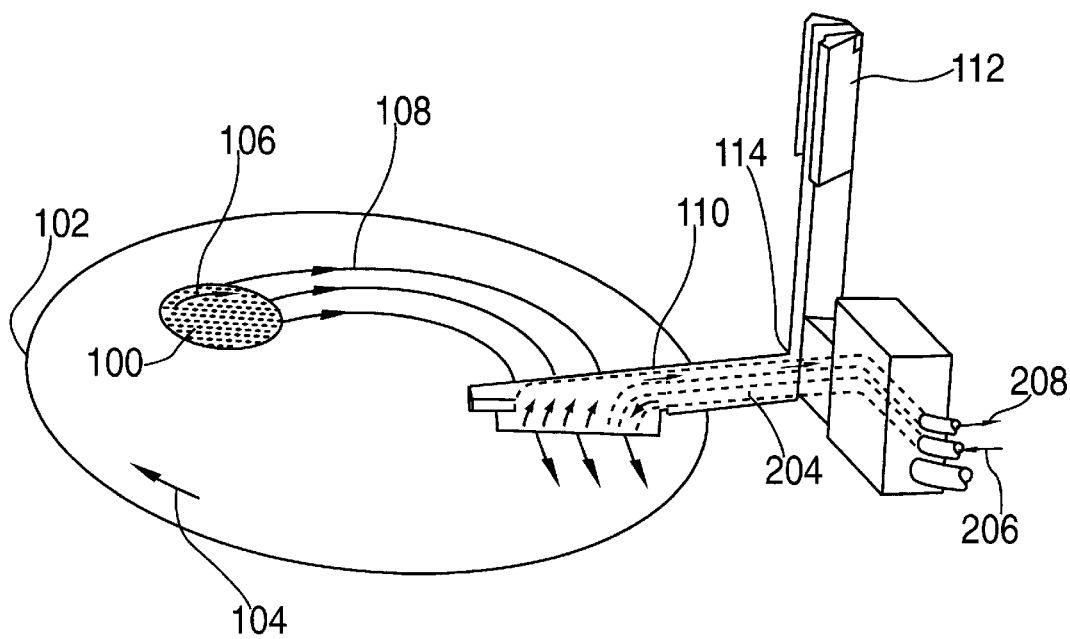
FIG. 1 shows the collection system in use in a CMP setup.

FIG. 1 shows the collection system in a chemical-mechanical polishing (CMP) setup. The underside of workpiece 100 (in this case, a semiconductor wafer) is being polished on a polishing pad 102 in the presence of a slurry. Note that the workpiece is typically held by some sort of carrier but the carrier is not shown for the sake of clarity. As shown, pad 102 rotates clockwise as shown by arrow 104. Wafer 100 also optionally rotates as indicated by arrow 106. Slurry is dispensed to pad 102 upstream or in front of wafer 100 and generally moves as indicated by arrows 108 downstream from or behind (i.e. clockwise from) wafer 100. Although a certain portion will fall off the edge of pad 102, an adequate amount stays on the pad for sampling at probe 110. The slurry that is to be sampled contains one or more gaseous reaction products that result from a chemical reaction between the slurry and the material being removed from the wafer, for example the layer(s) being polished. In order to collect and sample the reaction product, probe 110 is positioned in close proximity to the pad (and therefore will contact the slurry and possibly the pad).

Figure 2:
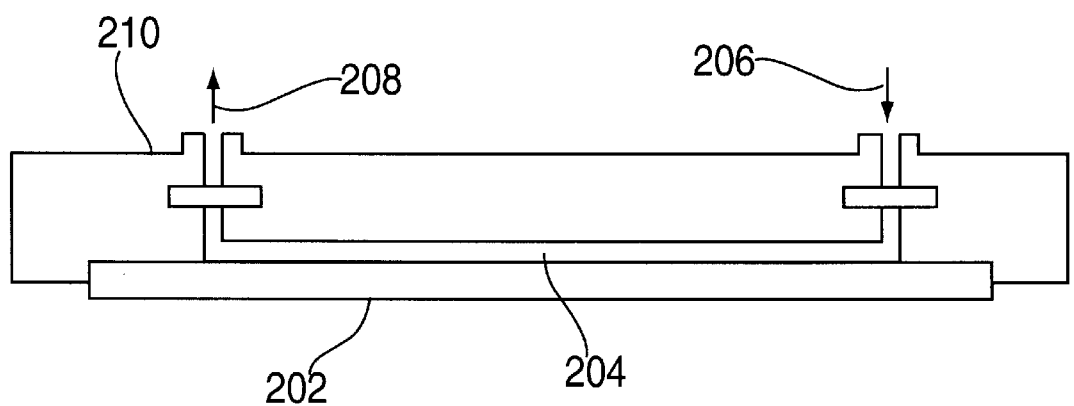
FIG. 2 shows a cross-section of the probe head; in accordance with the present invention.

FIG. 2 shows a cross-section of the probe that will contact the slurry. A membrane 202 separates the slurry from a channel 204. Membrane 202 is hydrophobic and permits only gas molecules to cross into channel 204, and acts as a barrier to the slurry on the pad. A carrier gas stream 206 (cleansed of any pre-existing amount of background gases that would interfere with the sampling and analysis to monitor the gaseous reaction product in the slurry) flows through channel 204 in the presence of a slight vacuum so that the pressure on the channel side of membrane 202 is lower than that on the outside (the slurry side). The pressure drop across the membrane ensures that an adequate amount of gaseous reaction product will flow into probe 108. Carrier gas stream 208 (now carrying the gaseous reaction product) then exits the probe head and is directed to an analyzer (not shown).

Downstream of membrane 202, another hydrophobic membrane 210 functions as a failure detector for membrane 202. Membrane 210 is designed so that if any fluid droplets do break through, they will be relatively large (e.g. approximately 2 mm in diameter). In the event that membrane 202 leaks or becomes damaged, fluid will flow to and partially block membrane 210. Thus a pressure drop will occur and can be detected by monitoring the carrier gas stream exiting the head of the probe. Detection of a pressure drop or of any fluid passing membrane 210 then activates a system which closes an inlet to the analyzer and stops the carrier gas flow.

In operation, as show in FIG. 1, probe 110 is in close proximity to (and possibly touching) the polishing pad, however it can be moved to alternate positions for servicing the probe or the polishing apparatus The probe is hinged at point 114 to enable this movement, and a locking mechanism ensures that the probe stays in the desired position. In a vertical position, the probe (and membrane) are protected by a shield 112 which closes around the probe. In this position, it is easy to change the polishing pad, and shield 112 protects the probe from being damaged.

The probe can also be fixed at a 45 degree angle so that the probe itself can be changed or maintained. Channel 204 is flexible at point 114 so that the probe can move between these positions.

In summary, a collection system for gaseous reaction products in a slurry for use in in-situ real-time sampling and analysis has been described, which is not affected by the slurry chemistry, does not interfere with the polishing process, and enables sampling with a rapid response time.

While the invention has been described in terms of specific embodiments, it is evident in view of the foregoing description that numerous alternatives, modifications and variations will be apparent to those skilled in the art. Thus, the invention is intended to encompass all such alternatives, modifications and variations which fall within the scope and spirit of the invention and the appended claims.

What is claimed is:

1. An apparatus for in-situ collection of a gaseous reaction product from a polishing slurry as a workpiece is being polished with the slurry, comprising:
   a probe capable of being placed in contact with the slurry, the probe having
      a channel for transmitting the gaseous reaction product to an analyzer,
      a first hydrophobic membrane for allowing passage of the gaseous reaction product from the slurry to the channel, and
      means for directing a carrier gas through the channel.

2. The apparatus of claim 1 further comprising a failure detector for the first hydrophobic membrane.

3. The apparatus of claim 2 further comprising means for stopping the flow of carrier gas in the event of a failure of the first hydrophobic membrane.

4. The apparatus of claim 1 wherein the workpiece is a semiconductor wafer, being polished with a chemical-mechanical polisher.

5. The apparatus of claim 4 wherein the probe is fixed to a polishing apparatus for polishing the semiconductor wafer, further comprising means for moving the probe between a position for contacting the slurry and a position for servicing the polishing apparatus.

6. The apparatus of claim 5 further comprising means for fixing the probe in a position for servicing the probe.

7. The apparatus of claim 1 wherein a pressure drop is created across the first hydrophobic membrane.

8. The apparatus of claim 1 further comprising a shield for protecting the probe while not in use.

9. A method for in-situ collection of a gaseous reaction product from a polishing slurry as a workpiece is being polished with the slurry, comprising the steps of:
   contacting the slurry with a probe, the probe having
      a channel for transmitting the gaseous reaction product to an analyzer,
      a first hydrophobic membrane for allowing passage of the gaseous reaction product from the slurry to the channel, and
      means for directing a carrier gas through the channel.

10. The method of claim 9 further comprising the step of creating a pressure drop across the first hydrophobic membrane.

11. The method of claim 9 wherein the workpiece is a semiconductor wafer, being polished with a chemical-mechanical polisher.

12. An apparatus for in-situ collection of a gaseous reaction product from a polishing slurry as a workpiece is being polished with the slurry, comprising
   a probe capable of being placed in contact with the slurry, the probe having
      a channel for transmitting the gaseous reaction product to an analyzer,
      a first hydrophobic membrane for allowing passage of the gaseous reaction product from the slurry to the channel, and
      means for directing a carrier gas through the channel,
   wherein the first hydrophobic membrane has a failure detector comprising a second hydrophobic membrane positioned in the channel downstream from the first hydrophobic membrane.

* * * * *